US 6,244,097 B1

(12) United States Patent
Schley et al.

(10) Patent No.: US 6,244,097 B1
(45) Date of Patent: Jun. 12, 2001

(54) METHOD FOR MEASURING WITHOUT COMBUSTION THE HEAT VALUE OF FUEL GAS

(75) Inventors: Peter Schley, Essen; Manfred Jaeschke, Dorsten; Reiner Kleinrahm, Bochum, all of (DE); Renee Janssen-van Rosmalen, Roden; Jan A. Schouten, Monnickendam, both of (NL)

(73) Assignees: N.V. Nederlandae Gasunie (NL); Ruhrgas Aktiengesellschaft (DE)

( * ) Notice: Subject to any disclaimer, the term of this patent is extended or adjusted under 35 U.S.C. 154(b) by 0 days.

(21) Appl. No.: 09/463,571

(22) PCT Filed: Aug. 20, 1998

(86) PCT No.: PCT/EP98/05304

§ 371 Date: Apr. 27, 2000

§ 102(e) Date: Apr. 27, 2000

(87) PCT Pub. No.: WO99/10740

PCT Pub. Date: Mar. 4, 1999

(30) Foreign Application Priority Data

Aug. 22, 1997 (DE) .............................................. 197 36 528

(51) Int. Cl.[7] .......................... G01N 25/00; G01R 27/26
(52) U.S. Cl. .................. 73/23.2; 73/23.21; 73/23.28; 73/30.01; 374/36; 702/30; 702/136
(58) Field of Search ................................. 73/23.2, 23.31, 73/24.01, 24.05, 23.28, 30.01, 597; 702/30, 27, 136; 374/36, 37; 436/143, 147

(56) References Cited

U.S. PATENT DOCUMENTS

| | | | | |
|---|---|---|---|---|
| 4,845,976 | * | 7/1989 | Johnson et al. | 73/23.2 |
| 5,182,523 | * | 1/1993 | Ertel et al. | 324/663 |
| 5,412,581 | * | 5/1995 | Tackett | 702/30 |
| 5,635,626 | * | 6/1997 | Hammond et al. | 73/23.2 |
| 5,932,793 | * | 8/1999 | Dayton et al. | 73/24.05 |

FOREIGN PATENT DOCUMENTS

4336174 * 4/1995 (DE).

OTHER PUBLICATIONS

"A Technology Assessment and Feasibility Evaluation of Natural Gas Energy Flow Measurement Alternatives Final Report, Tasks A and B", DE–FC21–96MC33033, Aug. 1998–Jan. 1999, 6 pages.

\* cited by examiner

*Primary Examiner*—Hezron Williams
*Assistant Examiner*—Michael Cygan
(74) *Attorney, Agent, or Firm*—Blakely Sokoloff Taylor & Zafman

(57) ABSTRACT

The fuel gas or a substream of the fuel gas is passed through a volumetric flowmeter and the volumetric gas flow is measured. In addition, the pressure, temperature and the proportion of at least one inert gas as well as the density and the dielectric constant are measured under reference conditions. The amount of heat supplied to gas consumption devices can be determined from these six parameters reliably without complicated technology.

13 Claims, 4 Drawing Sheets

METHOD FOR MEASURING WITHOUT COMBUSTION THE HEAT VALUE OF FUEL GAS

The present invention relates to a non-combustive method for measuring the gross calorific value of fuel gas and to a use of the method for the non-combustive measurement and/or regulation of the amount of heat supplied to gas consumption devices, in particular to devices for consumption of natural gas.

The advantage of non-combustive methods for measuring the gross calorific value or measuring the amount of heat compared with calorimetric methods in which controlled combustion of a substream of the gas stream being transferred is carried out is that they are significantly cheaper. However, practical implementation is frequently complicated, quite apart from the difficulties which can occur in calibration.

Non-combustive methods of measurement include indirect and correlative methods. With the indirect methods, the gas composition is analysed. The composition of the gas together with the gross calorific values for the pure substances can then be used to determine the gross calorific value of the fuel gas. These methods (e.g. gas chromatography) give very accurate results, but the technology is complicated and therefore they are not very suitable for use in, for example, the residential sector. In addition, they are prone to faults.

With the correlative methods for measuring the gross calorific value or the amount of heat, a relationship between a readily measurable physical or chemical parameter and the gross calorific value is exploited. This makes them easier to perform from the technical point of view, but the reproducibility and the accuracy of the measurement of the gross calorific value or the amount of heat are restricted to an undesirable degree.

It is an object of the present invention to make the correlative non-combustive measurement of the gross calorific value or the measurement and/or regulation of the amount of heat supplied to consumption devices less complicated and, in particular, to provide a reliable and accurate measuring method.

This object is achieved according to the invention by the characterising features of claim 1.

In practice there are different time-tested methods for measuring the density under reference or operating conditions. The speed of sound under reference or operating conditions can be determined in a separate measuring unit, for example, via the resonant frequency of pipes or of hollow bodies or a distance travelled-time measurement e.g. in ultrasonic flowmeters. The dielectric constant can be measured inexpensively and with high accuracy even under operating conditions.

Consequently, the two measurements required in each case can be carried out without complicated technology, reliably and accurately so that the combination of the measured values gives corresponding results for the gross calorific value. The gross calorific value determined in this way can be used, for example, for controlling combustion processes.

Depending on the application, it is possible to determine the gross calorific value on a volume basis under reference or operating conditions, the specific gross calorific value (on a mass basis) or the molar gross calorific value.

There are a total of four variations of the method of the invention for measuring the gross calorific value of fuel gas. In the first variant, the density and the dielectric constant are measured under reference conditions and in the second variant the speed of sound and the dielectric constant are measured under reference conditions. These two variants have the advantage that the measuring apparatus working under reference conditions is cheap to buy and simple to maintain.

In the third variant, the density and the dielectric constant are measured under operating conditions and in the fourth variant the speed of sound and the dielectric constant are measured under operating conditions. The advantage of these last two variants is that no thermostats are required to establish the reference conditions. Finally, in the third and fourth variants no pressure reductions are required to establish normal reference conditions.

However, the measuring equipment to measure the dielectric constant and the density or speed of sound under operating conditions is somewhat more expensive to purchase than the measuring equipment for the first two variants. Furthermore, the evaluation of the parameters to determine the gross calorific value is more difficult in the last two variants of the inventive method for measuring the gross calorific value than in the first two variants.

To find a suitable correlation between the measured parameters and the gross calorific value, it is advantageous to precede the respective steps a) and b) at least once by a plurality of measurement cycles in which step a) is carried out using a plurality of reference gases of known gross calorific value. The parameters required for the various variants of the method are then measured on the reference gas. In these reference cycles, a number of reference signal patterns corresponding to the number of measurement cycles determined from the ratio of the various signals measured is stored with assignment to the known gross calorific values. The signal pattern from a future measurement cycle on fuel gas of unknown gross calorific value is compared with reference signal patterns for the purposes of establishing a particular gross calorific value.

To increase the reference accuracy, a large number of reference cycles in which the various parameters are varied in succession over the expected measurement range should be carried out. An unambiguous and accurate assignment of a particular gross calorific value to a signal pattern of a fuel gas determined in a measurement cycle is achieved by interpolation of the various reference signal patterns.

A significant advantage is that the correlation between gross calorific value and measured parameters only has to be found once for a specific application by means of any desired number of reference cycles. The one-off work involved is comparatively small. The reference conditions should here be selected so as to correspond as closely as possible to the measurement conditions expected later. Thus, for all parameters only the measurement ranges which actually come into question should be determined with sufficient accuracy as reference signal patterns.

The dielectric constant and the density or the speed of sound are preferably measured under reference conditions in a common measuring environment. This makes only one temperature and pressure measurement and consequently only one thermostat necessary for setting and maintaining the reference conditions. Furthermore, uniform reference conditions for the measurement of the dielectric constant and the density increase the accuracy to which the amount of heat supplied can be determined.

One advantageous embodiment is characterised in that normal conditions are set as reference conditions for the measurement of the density or the speed of sound and/or the dielectric constant.

The dielectric constant can be measured particularly accurately at a reference pressure of at least 1 MPa.

The accuracy with which the gross calorific value is measured can be further increased by also measuring in step a) at least one of the parameters temperature, pressure or the proportion of at least one inert gas, preferably the proportion of carbon dioxide. Naturally, the highest measuring accuracy can be obtained if all three parameters are also measured.

A further embodiment of the present invention is characterised in that a substream of the fuel gas is taken off for the measurement of the density or the speed of sound under reference conditions and that the proportion of at least one inert gas, preferably the proportion of carbon dioxide, is measured on this substream, preferably after the density or the speed of sound have been measured.

The object of the invention is also achieved by the use of the novel non-combustive method of measuring and/or regulating the amount of heat supplied to gas consumption devices, in particular devices for consumption of natural gas, wherein, in step a), the fuel gas or a substream of the fuel gas is additionally passed through a volumetric flowmeter or mass meter and the volume or the mass of the fuel gas supplied is measured.

For the purposes of the present invention, gas consumption devices are all necessary devices for the use of gas on the premises of private and industrial customers and also all transfer points or the like.

According to the invention, it is possible, for example, for the amount of heat supplied to residential premises to be derived from only three parameters, namely firstly the volume or the mass, secondly the dielectric constant and thirdly the density or speed of sound under reference or operating conditions. The technical work involved and the cost of this are minimal.

To increase the accuracy, it is possible, as in the measurement of the gross calorific value, to determine as many further parameters as desired. For applications in which particularly high measurement accuracies are required, e.g. for determining the amount of heat supplied at transfer points of main transmission lines with a high gas throughput, it is advantageous to measure the pressure, the temperature and the proportion of carbon dioxide in addition to the above three parameters.

In the following, the use of the novel non-combustive method for measuring and/or regulating the amount of heat supplied to gas consumption devices is illustrated by means of the embodiments shown in the drawing.

Figure 1:
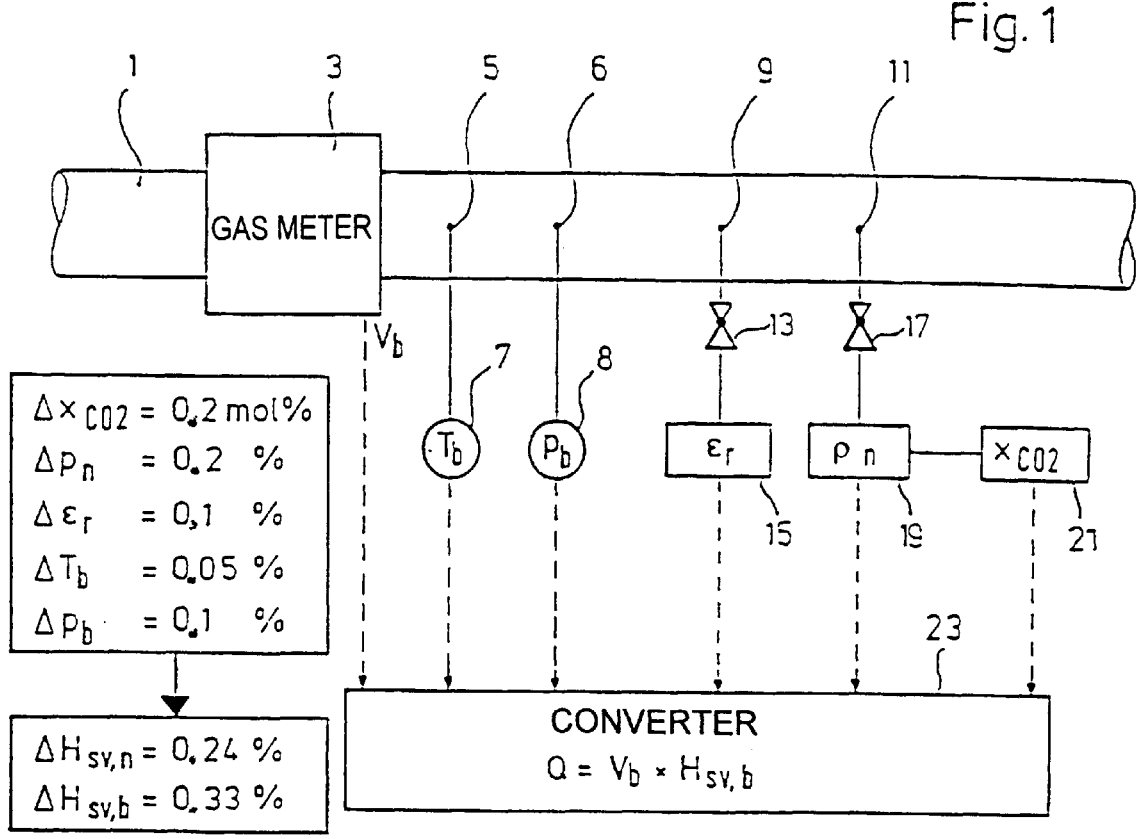
FIG. 1 shows a schematic view of an arrangement for carrying out a first embodiment of the use according to the invention of the method for measuring the gross calorific value.

FIG. 1 shows a fuel gas line 1 in which a gas mete, 3 is located. In addition, two measurement points 5 and 6 are located in the fuel gas line 1. Measurement point 5 is provided with a temperature sensor 7 and measurement point 6 is provided with a pressure sensor 8. Furthermore, two offtake points 9 and 11 are provided in the fuel gas line. Offtake point 9 is connected via a pressure-reducing valve 13 to a measuring device for measuring the dielectric constant 15. Offtake point 11 is connected via a pressure-reducing valve 17 to a measuring device for measuring the density 19. The measuring device 19 is connected via a fuel gas line to a measuring device 21 to determine the proportion of carbon dioxide.

The signal outputs of the gas meter 3, the temperature sensor 7, the pressure sensor 8 as well as the measuring devices 15, 19 and 21 are connected to the inputs of a converter 23.

In the operating condition, the gas meter 3 measures the volumetric flow of gas and the time and calculates from these two figures the volume of fuel gas supplied. The sensor 7 measures the temperature and the pressure sensor 8 measures the pressure in the fuel gas line 1. The measuring device 15 measures the dielectric constant under reference conditions, namely, for example, at a pressure of 1 bar and a temperature of 288.15 K. Density is measured in a measuring device 19 under normal conditions. After the density has been measured, the proportion of carbon dioxide is measured on the fuel gas substream removed at offtake point 11. All measured values are sent to the converter 23. Said converter calculates the gross calorific value under operating conditions $H_{SV,b}$, first of all by correlation. Then the converter 23 calculates the amount of heat Q by multiplying the gross calorific value $H_{SV,b}$ by the volume under operating conditions $V_b$.

Figure 2:
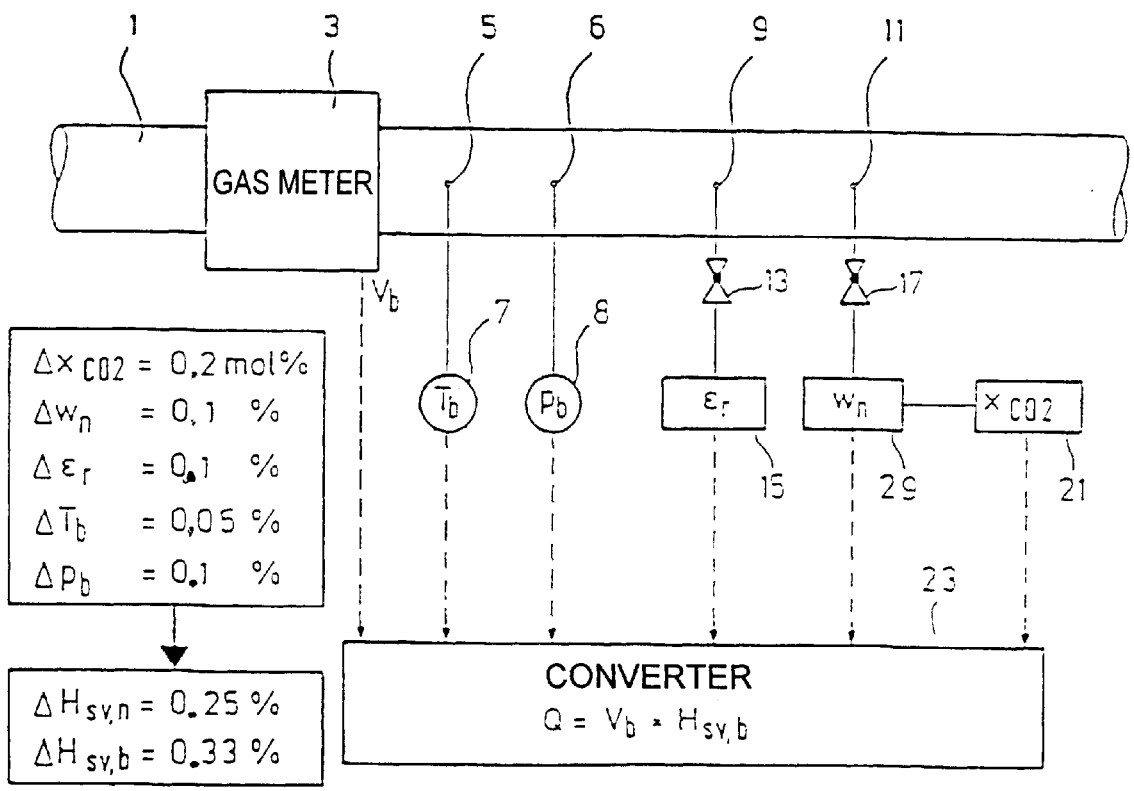
FIG. 2 shows a schematic view of an arrangement for carrying out a second embodiment of the use according to the invention.

FIG. 2 shows an arrangement for carrying out a second embodiment of the invention. The arrangement in FIG. 2 differs from the arrangement in FIG. 1 only in that a measuring device 29 for measuring the speed of sound under normal conditions is provided instead of the measuring device 19 for measuring the density. The amount of heat is calculated by the converter 23 in this embodiment of the present invention on the basis of the volume, the temperature and the pressure under operating conditions, the dielectric constant under reference conditions, the speed of sound under normal conditions and the proportion of carbon dioxide.

Since in both the embodiments shown in FIG. 1 and FIG. 2 the measurement devices for the dielectric constant, the speed of sound and the pressure are located outside the fuel gas line, maintenance of said apparatus and any repair can be carried out without any particular technical problem. In addition, only comparatively few reference cycles are required, since the dielectric constant and the speed of sound are measured under specified conditions. There is thus a direct correlation between a change in the dielectric constant and the speed of sound or the density and a change in the gas composition. The embodiment shown in FIG. 2 can be realised particularly inexpensively since the speed of sound is simpler and cheaper to measure than the density of the fuel gas.

Figure 3:
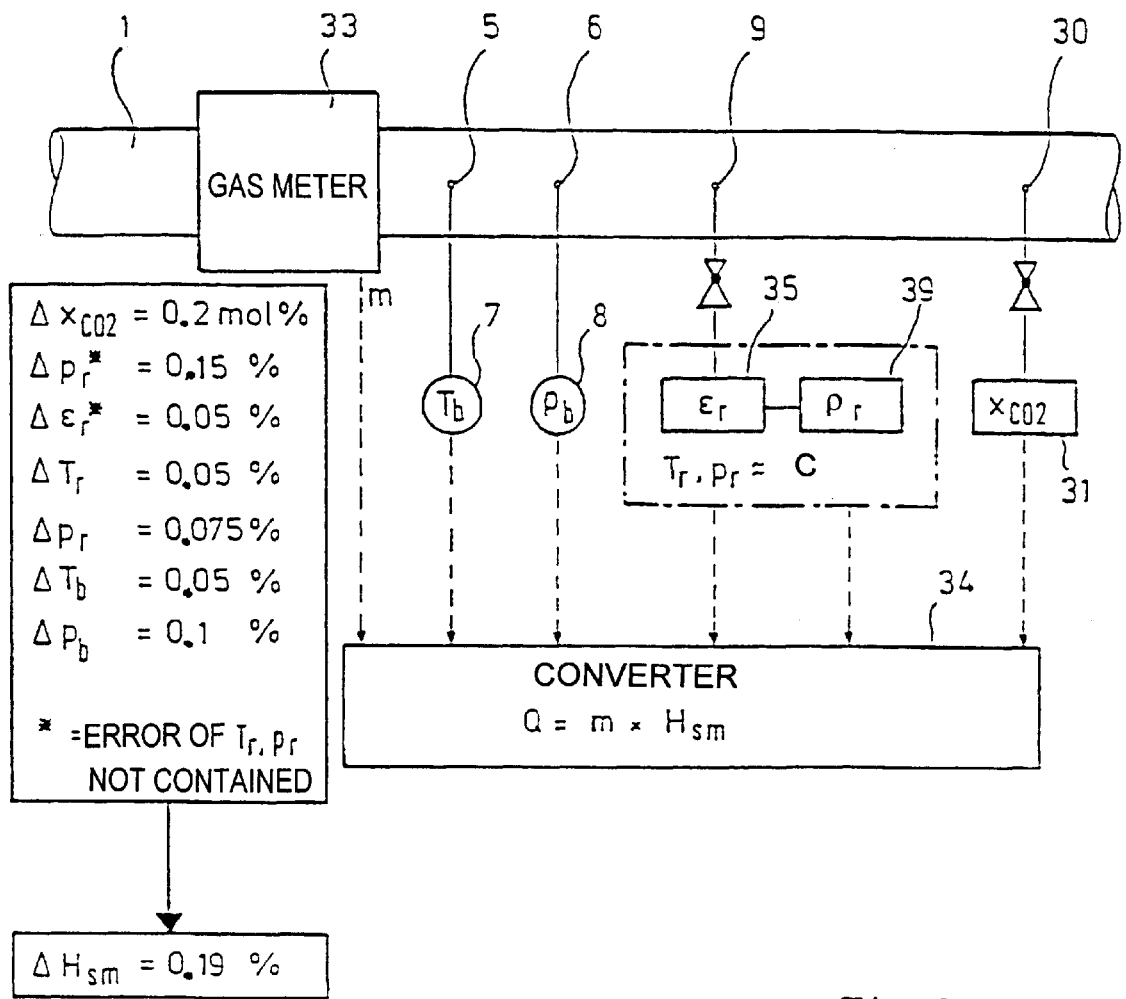
FIG. 3 shows a schematic view of an arrangement for carrying out a third embodiment of the use according to the invention.

FIG. 3 shows a third embodiment of the invention. The arrangement shown in FIG. 3 differs from the arrangement shown in FIG. 1 in that a mass meter 33 for measuring the mass of the fuel gas supplied is provided instead of the volumetric flowmeter. Furthermore, a separate offtake point 30 is assigned to the measuring device for determining the proportion of carbon dioxide 31. In addition, the metering device for measuring the dielectric constant 35 and for measuring the density 39 are arranged in a common measuring environment in which a preset temperature and a preset pressure prevail.

The corrector 34 first calculates the gross calorific value Hsm by correlation. Subsequently, the energy translator 34 calculates the amount of heat Q by multiplying the gross calorific value $H_{Sm}$ by the mass m.

Figure 4:
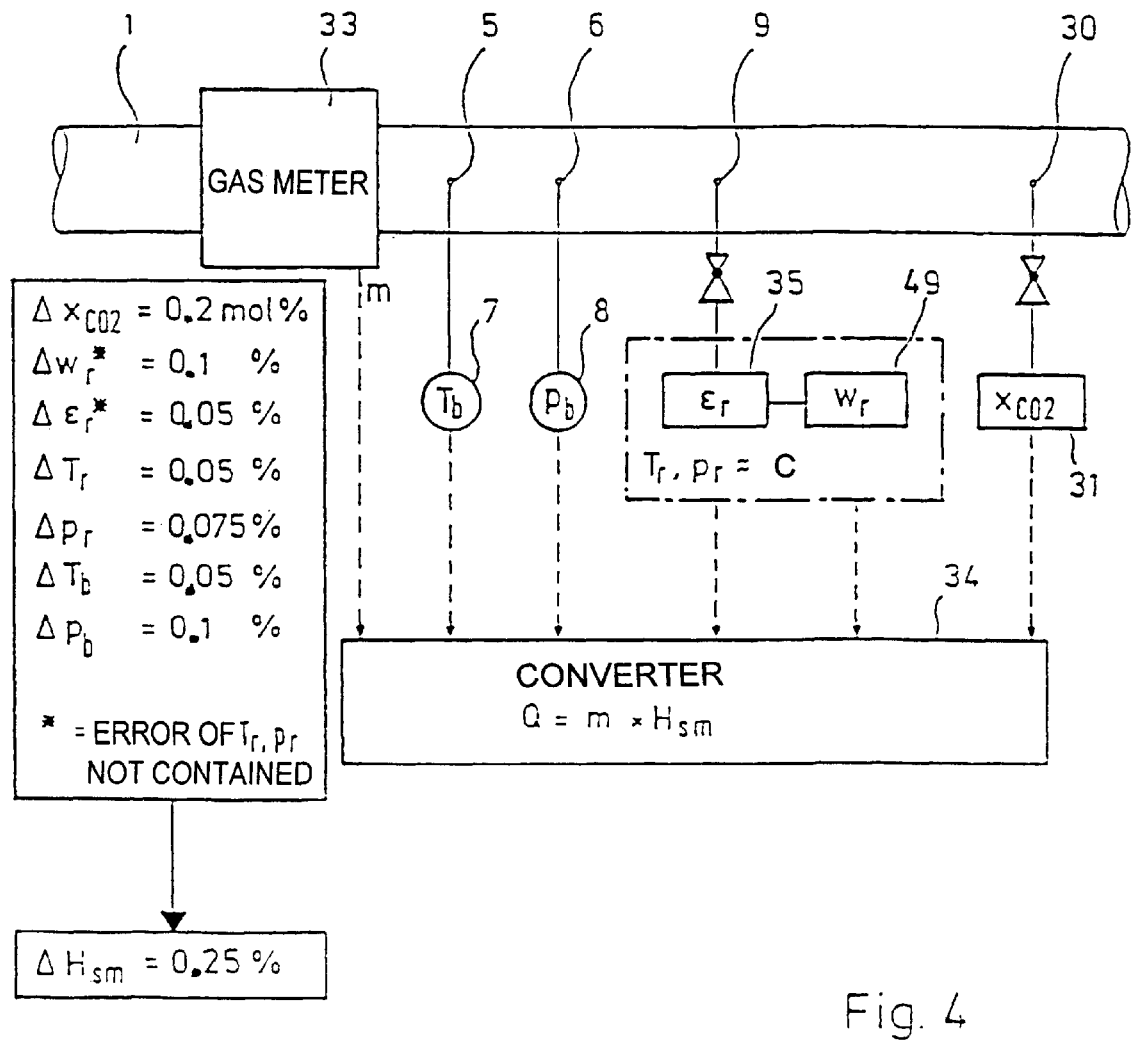
FIG. 4 shows a schematic view of an arrangement for carrying out a fourth embodiment of the use according to the invention.

In the fourth embodiment of the invention shown in FIG. 4, the only difference between the third embodiment shown in FIG. 3 is that a measuring device for measuring the speed of sound 49 in the common measuring environment is provided instead of a measuring device for measuring the density 39.

Like the first two embodiments, the third and the fourth embodiments have the advantage that only a few reference cycles have to be carried out to reliably determine the amount of heat. Furthermore, the advantage of the common measuring environment for measuring the dielectric constant and the density or speed of sound is that only one pressure and temperature measurement is required in addition to the pressure and temperature measurement in the fuel gas line. In contrast to the two first embodiments, it is also not necessary to provide a thermostat. The third embodiment is particularly accurate in the determination of the amount of heat and is therefore particularly advantageous.

Figure 5:
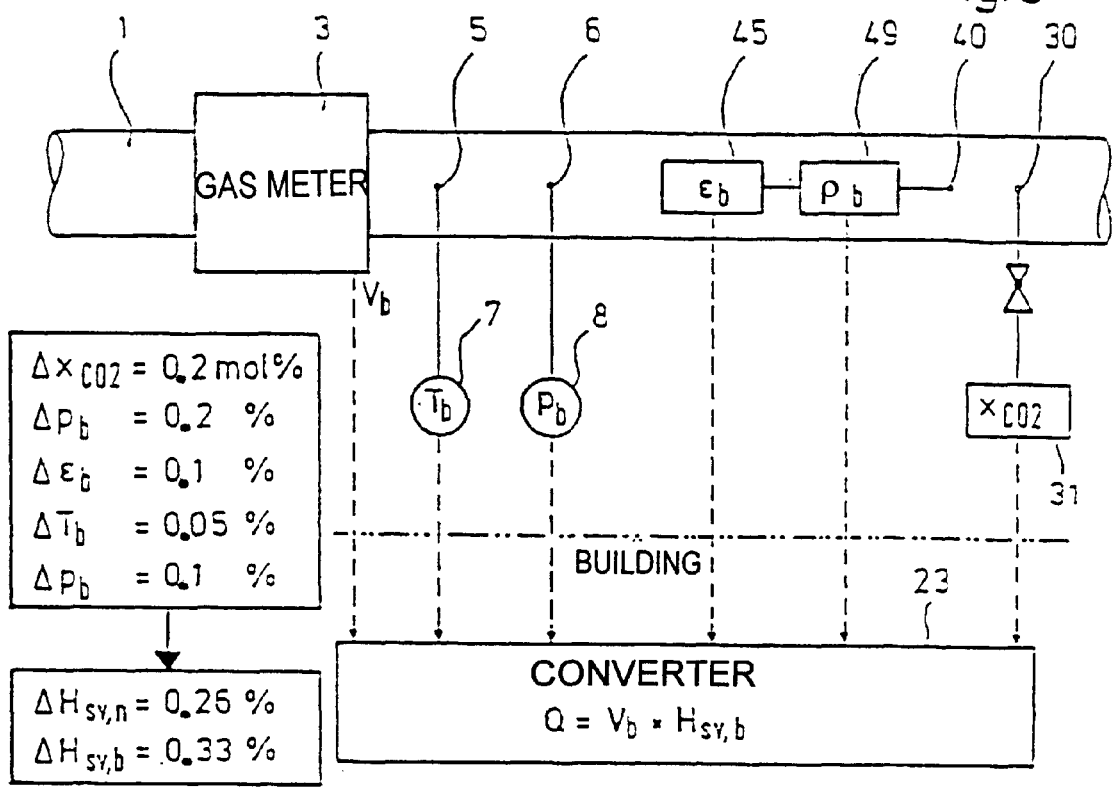
FIG. 5 shows a schematic view of an arrangement for carrying out a fifth embodiment of the use according to the invention.

FIG. 5 shows a fifth embodiment of the invention. The arrangement in FIG. 5 only differs from the arrangement in FIG. 3 in that a measurement point 40 is provided in the fuel gas line, a measuring device 45 for determining the dielectric constant under operating conditions and a measuring device 49 for determining the density under operating conditions being assigned to said measurement point 40. All parameters, apart from the proportion of carbon dioxide, are measured under operating conditions in this particular embodiment. Furthermore, the volume is measured instead of the mass measured in the embodiments in FIGS. 3 and 4. The parameters volume, temperature, pressure, dielectric constant and density under operating conditions are then transmitted to the converter 23.

Figure 6:
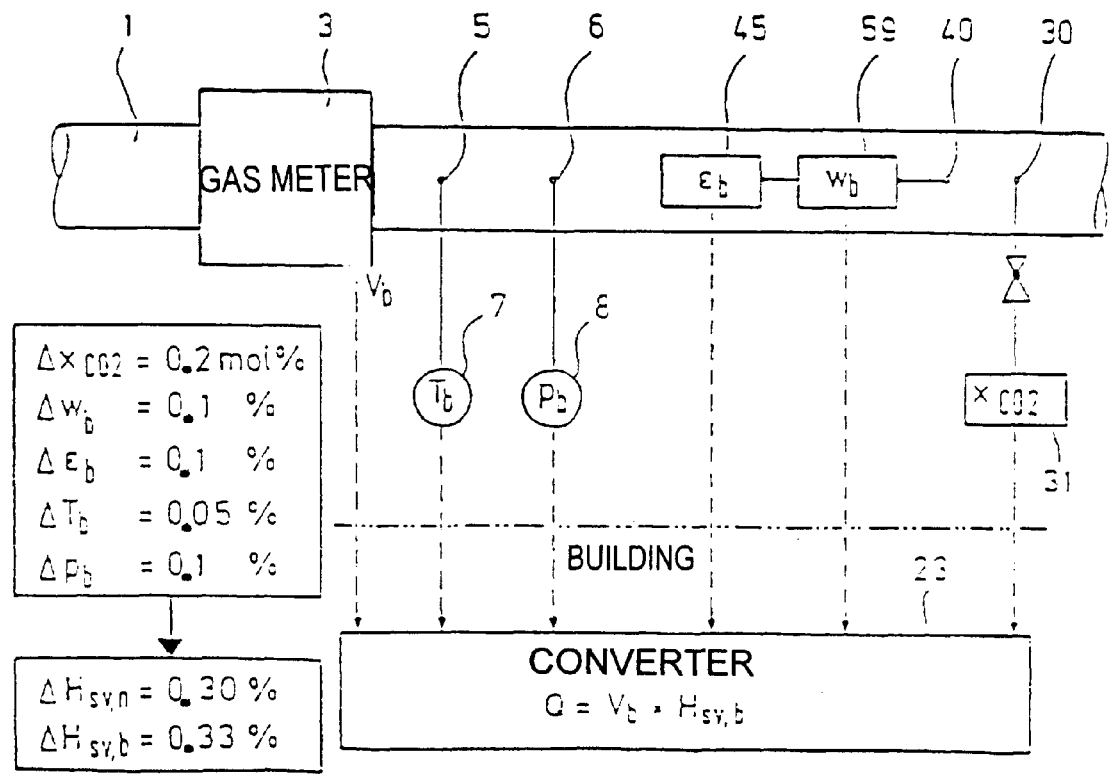
FIG. 6 shows a schematic view of an arrangement for carrying out a sixth embodiment of the use according to the invention.

FIG. 6 shows a sixth embodiment of the invention. The arrangement in FIG. 6 only differs from the arrangement in FIG. 5 in that in the fuel gas line 1 a measuring device 59 for measuring the speed of sound is provided instead of the measuring device 49 for measuring the density.

The advantage of the fifth and the sixth embodiments is that no reference conditions have to be set since the dielectric constant and the density or speed of sound are measured under operating conditions. Thus the arrangement is simpler in that thermostats can be dispensed with.

In addition, the temperature and pressure sensors required for setting the reference conditions can be completely dispensed with. A reduction in the pressure is only necessary to determine the proportion of carbon dioxide in the measuring device 31. Finally the embodiments in FIG. 5 and FIG. 6 have the advantage that the method can be performed outdoors as all measuring equipment is directly assigned to the fuel gas line. In the embodiments shown, the measuring devices are connected via signal lines to the converter 23 located in a building. The space requirement to perform the inventive method is very low for these two embodiments.

Further embodiments are possible within the scope of the present invention. In particular the time sequence of the measurements for determining the various parameters can be varied at will. The reference conditions can also be freely selected. Finally, not only the dielectric constant and the density or speed of sound but also the proportion of carbon dioxide can be measured in the common measuring environment.

What is claimed is:

1. A method comprising:
 measuring the amount of heat supplied to a gas consumption device, comprising:
 I. providing a plurality of reference measurement cycles using a plurality of reference gases each of the plurality of reference gases having a predetermined gross calorific value, wherein
  a) a first one of the plurality of reference measurement cycles including: measuring the dielectric constant of a first reference gas and a selected physical variable of the first reference gas, under conditions selected from first and second conditions with the first conditions being reference conditions and the second conditions being operating conditions;
  b) repeating operation a) on the remainder of the plurality of reference gases for carrying out the other reference measurement cycles;
  c) recording a number of reference signal patterns corresponding to the number of the reference measurement cycles, the reference signal patterns determined from a ratio of various measurement signals obtained by operations a) and b);
  d) storing the reference signal patterns with assignment to the predetermined gross calorific values of the plurality of reference gasses;
 II. performing at least one measuring cycle on a fuel gas supplied to the gas consumption device, the fuel gas measuring cycle comprising:
  a) measuring the dielectric constant of the fuel gas and a selected physical fuel gas variable selected from first and second conditions with the first conditions being reference conditions and the second conditions being operational conditions;
  b) providing a new measurement signal pattern including the two measurement signals derived from operation II.a);
  c) comparing the new measurement signal pattern obtained from operation b) on the fuel gas of unknown gross calorific value with the reference signal patterns as stored in operation I.d) and deriving the gross calorific value of the fuel gas from this comparison;
 III. passing at least a substream of the fuel gas supplied to the gas consumption device to a quantity meter, to measure the quantity of the fuel gas supplied to the gas consumption device,
 wherein the amount of heat delivered to the consumption device can be derived from a combination of the gross calorific value obtained in operation II.c) and the quantity measurement obtained in operation III.

2. The method of claim 1, wherein the selected physical variable of the fuel gas is one of density, and the speed of sound of the reference gas.

3. The method of claim 1, wherein the quantity meter is one of a volumetric flow meter and a mass flow meter.

4. The method of claim 1, wherein the dielectric constant and the selected physical variable are measured under reference conditions in a common measuring environment.

5. The method of claim 1, wherein normal conditions are set as reference conditions for the measurement of the density of the gas.

6. The method of claim 1, wherein normal conditions are set as reference conditions for the measurement of the speed of sound of the gas.

7. The method of claim 1, wherein normal conditions are set as reference conditions for the measurement of the dielectric constant.

8. The method of claim 1, wherein a reference pressure of at least 1 MPa (~10 atmospheres) is set as the reference condition for the measurement of the dielectric constant.

9. The method of claim 1, wherein in operations a) at least one of the parameters selected from the temperature, pressure, and the proportion of at least one inert gas is also measured.

10. The method of claim 9, wherein a substream of the fuel gas is taken off for measurement of at least one of the density and of the speed of sound under reference condition and that the proportion of at least one inert gas is measured on the substream.

11. The method of claim 10, wherein the at least one inert gas is carbon dioxide.

12. The method of claim 1, where in at least a substream of the fuel gas is passed through a volumetric flow meter to measure the volume of gas supplied to the consumption device.

13. The method of claim 1, where in at least a substream of the fuel gas is passed through a mass meter to measure the mass of gas supplied to the consumption device.

* * * * *

UNITED STATES PATENT AND TRADEMARK OFFICE
CERTIFICATE OF CORRECTION

PATENT NO. : 6,244,097 B1
DATED : June 12, 2001
INVENTOR(S) : Schley et al.

Page 1 of 1

It is certified that error appears in the above-identified patent and that said Letters Patent is hereby corrected as shown below:

<u>Title page,</u>
Item [73], delete "Nederlandae" and insert -- Nederlandse --.

<u>Column 8, claim 13,</u>
Line 11, delete "ma ss" and insert -- mass --.

Signed and Sealed this

Eighth Day of January, 2002

Attest:

JAMES E. ROGAN
*Attesting Officer*     *Director of the United States Patent and Trademark Office*